(12) United States Patent
James (10) Patent No.: US 7,302,297 B2
(45) Date of Patent: Nov. 27, 2007

(54) APPARATUS FOR APPLYING PULSED CHARGE TO LIVING MATTER

(76) Inventor: Robert G. James, 205 Westlake Ct., Niceville, FL (US) 32578

( * ) Notice: Subject to any disclaimer, the term of this patent is extended or adjusted under 35 U.S.C. 154(b) by 398 days.

(21) Appl. No.: 11/117,560

(22) Filed: Apr. 28, 2005

(65) Prior Publication Data

US 2005/0209660 A1 Sep. 22, 2005

Related U.S. Application Data

(63) Continuation-in-part of application No. 10/798,036, filed on Mar. 11, 2004, now Pat. No. 7,130,698.

(51) Int. Cl.
*A61N 1/00* (2006.01)

(52) U.S. Cl. .................. 607/115; 607/96; 607/101; 606/32; 606/33

(58) Field of Classification Search .......... 607/96–101, 607/115; 606/32–35, 41
See application file for complete search history.

(56) References Cited

U.S. PATENT DOCUMENTS

| | | | | |
|---|---|---|---|---|
| 5,184,046 A | * | 2/1993 | Campbell | 315/111.21 |
| 5,300,097 A | * | 4/1994 | Lerner et al. | 607/93 |
| 6,328,760 B1 | * | 12/2001 | James | 607/88 |
| 7,130,698 B2 | * | 10/2006 | James | 607/115 |

* cited by examiner

*Primary Examiner*—A. Farah
(74) *Attorney, Agent, or Firm*—I. Michael Bak-Boychuk (57) ABSTRACT

Apparatus for inducing electrically charged alignment changes in biological tissue includes a generally flat translucent cavity containing a volume of gas that includes water vapor, carbon dioxide and other similarly common molecules that is charged along one surface by a sequence of pulses of electrical charge each of a potential sufficient to excite the common molecules to a higher state. The opposite side of the cavity is then conformed for intimate contact with the skin of a person, thus communicating the right hand spin electromagnetic pulses associated with each excitation level change into the tissue. A pulsed coil is then provided in an alignment generally parallel to the plane of the cavity to polarize the clockwise electromagnetic emissions associated with the changes in the excitation states.

12 Claims, 6 Drawing Sheets

FIG. 1

PRIOR ART

APPARATUS FOR APPLYING PULSED CHARGE TO LIVING MATTER

REFERENCE TO RELATED APPLICATIONS

This application is a continuation in part of U.S. patent application Ser. No. 10/798,036 filed 11 Mar. 2004, now U.S. Pat. No. 7,130,698, and benefit of this earlier filing date is claimed for all matter common therewith.

BACKGROUND OF THE INVENTION

1. The Technical Field

The present invention relates to pulsed charge devices, and more particularly to charged surfaces coupled to anatomical parts polarized to a right hand clockwise spin by a pulsed electromagnetic field to induce electron state changes in the biological matter.

2. The Prior Art

In my prior U.S. Pat. No. 6,328,760 issued on Dec. 11, 2001 I have described a plasma device conformed to ionize certain prevalent biological elements and molecules with the emission spectra of this ionization process then coupling efficiently with the dominant element and molecular structures in living matter. In consequence, repair and reconstruction of living cells is both accelerated and enhanced by the illumination with these selected spectra. Since that time I have discovered that a filly developed ionization process need not be utilized and an electrical potential between the living matter and the charge sufficient to change some of the electron states of the molecular combinations of living tissue may produce the necessary molecular lattice rearrangement to promote growth or healing.

Earlier I and others have observed that virtually all living functions entail electrical potential balances and the cell itself closely mimics a 'wet circuit'. Sporadic disruptions of these potential balances, either because of the introduction of some contaminant or as result of some unwanted change in the charge architecture, seem to be the causative events that lead to disease and it is the rearrangement of this charge architecture anomalies that appear to be at the heart of the process that I earlier described in the '760 us patent. Of course, excepting those abnormalities that reach into the genome itself most of these electro-potential effects seem to be at the larger or macro level, such as those affecting the Na+/K+ pump, and the excitation of just some of the more basic molecules appears to be sufficient to assist in rearranging the other charge architectures back to their normal states.

The foregoing effect appears to have some confirmation in scientific literature. For example, Horwitz, L R, Burke, T J, Carnegie, D, 1999. Augmentation of Wound Healing Using Monochromatic Infrared Energy; Exploration of a New Technology for Wound Management. *Advances in Wound Care* 12:35-40 describes the use of 890 nanometer monochromatic light effectively treating recalcitrant dermal lesions and ulcers that sometimes resisted conventional care for more than 39 years. Similarly, living tissue molecular array response to weak electric and magnetic fields has long been recognized. See, e.g., Adey, W R, Bawin, S M Brain Interactions with Weak Electric and Magnetic Fields. *Neurosciences Research Program Bulletin* 15(1):1-129. These and other publications clearly establish an interactive relationship between living tissue and weak electromagnetic fields.

Notably, however, this same effect is also associated with emission of light in unique and distinct spectral patterns with a symmetrical result then obtained by absorption of the light energy in similar molecular structures illuminated thereby. In the bulk tissue structure this interchange is polarity dependent obtainable in an electromagnetic right hand spin polarizing field which may be overlayed over the emitting source. Accordingly, a mechanism for conveniently producing such right hand spin polarized emission fields that induce response in living tissue including electron state changes is extensively desired and it one such mechanism that is disclosed herein.

SUMMARY OF THE INVENTION

Accordingly, it is the general purpose and object of the present invention to provide a pulsed charge field contained in an electromagnetic field conformed for raising the excitation states of molecular bonding in biological molecules.

Other objects of the invention are to provide a pulsed charge field including frequency spectra in each pulse within the frequency domain of a wet circuit.

Yet further objects of the invention are to provide a pulsed charge circuit completed through the charge architecture of living matter.

Further objects of the invention are to provide a conveniently implemented electrical charge field in circuit with the wet circuit charge architecture of living matter.

Yet additional objects of the invention are to provide a right hand spin polarizing electromagnetic field superposed onto a charge field conformed to raise the excitation state of biological matter.

Briefly, these and other objects are accomplished within the present invention by providing a direct current powered oscillator circuit transformer coupled to a plurality of voltage doubler stages connected to the positive charge terminal that is shaped in the form of a flat plate. The plate, in turn, is enclosed on the exterior surface of a generally flat gas filled chamber that can be pressed to the selected limb or body area of a person with the local charge differential across the chamber then providing localized electrical potentials which effect an energy state change in the gas along with the associated radiation. By selecting a molecular structure of the gas similar to the molecular structures in the adjacent tissue a part of the emitted radiation is then absorbed in the adjacent molecular arrays of the body, raising the excitation levels in the tissue which propagate until a local equilibrium is reached. This equilibrium includes the ambient setting through which the ground return part of the circuit is completed, with the lack of observable radiation then providing an indication that the circuit impedance may be too high, i.e., that the contact skin area may be too dry. In this manner the polar molecules that are associated with all living tissue are included in the circuit lattice responding both to the electrical potential and to the gas emitted radiation.

The radiated emissions thus produced can then be further controlled by a superimposed electromagnetic field produced on the interior of a coil surrounding the flat negatively charged plate and the chamber on which it is fixed. A further pulse circuit may then be connected across the coil, thus exciting the electromagnetic field to its selected pulse frequency. As result the emissions in the chamber are uniformly right hand spin polarized along their vectors that coincide with the field vector within the coil, thus insuring a relatively uniform absorption within the generally polar architecture of the molecular lattice that forms the irradiated tissue.

Those skilled in the art will appreciate that virtually all organic molecules are associated with a distributed electrical charge. Very frequently it is this charge distribution that determines the lobes and foldings of the larger molecules like proteins or peptides and it is the occasional distortions in this charge determined geometry that is often the suspected causative agent associated with disease. Simply, the lobe architecture of a large molecule may be altered by external effects which then alters the molecular interactions with, e.g., receptors, until rearranged to equilibrium state. Of course, the disease consequence associated with distortions in our largest molecules, the chromosomes, are well appreciated at this time and fundamental reasoning dictates that the adjacent smaller molecules will invariably have some effect across the whole range of molecular sizes. It is this effect that is conveniently allowed to resolve itself by the inventive structure disclosed herein.

DESCRIPTION OF THE PREFERRED EMBODIMENT

Figure 1:
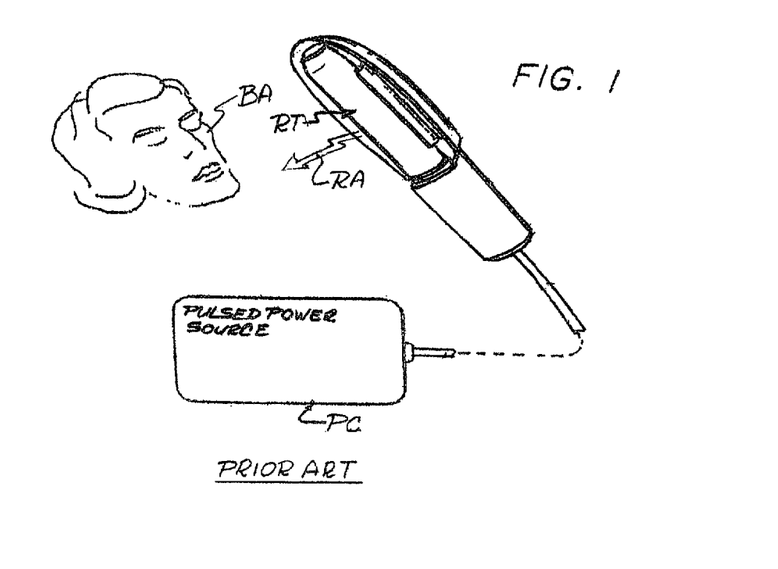
FIG. 1 is a perspective illustration of a prior art gas discharge device useful in emitting light in biologically significant spectra.

By reference to FIG. 1 my prior U.S. Pat. No. 6,328,760 teaches a pulsed plasma radiation tube RT excited by a pulse circuit PC to ionization potential of the gases contained therein selected to emit radiation RA in biologically significant spectra onto the treated body area BA of a user. To achieve this radiation the gas within the plasma tube RT included molecules like water vapor or $H_2O$, carbon dioxide $CO_2$, molecular nitrogen $N_2$ and perhaps carbonic acid $H_2CO_3$ all driven to ionization by the pulse circuit PC. The resulting radiated spectra were then useful in exciting illuminated tissue containing corresponding molecules, or loosely bound components of larger molecules like peptides or proteins, and the higher energy states of these excited elements and molecules would induce, in the manner of a cascade, further state changes propagated through the wet circuit of a cell. In this propagation process any molecular distortions or electrical charge misalignments would be freed up to return to their preferred state. These molecular rearrangement by this negatively ionized gas spectral illumination process have resulted in substantial molecular responses, both useful in promoting healing and in the maintenance of proper homeostasis.

While suitable for the purposes intended and widely useful in the care of various diseases I have since found that the higher potentials of full ionization are not necessary and, in stead, only a sufficient charge difference to obtain an electron state response need be applied. Although not fully understood, it appears that the lattice of polar molecules that are included in all living tissue provides its own charge distributions at the body surface and this distribution may be used to advantage in producing sufficient electric potential to effect an electron state change. Of course, this is associated with a release of radiation which then raises the state of other electrons and this state change then cascades down into the treated tissue through its molecular lattice until all the available state changes can be effected, and so on. In this manner large body areas can be influenced with relatively low electric potentials.

This lower level of charge differential can be conveniently effected by modifying the pulse circuit of my earlier U.S. Pat. No. 6,328,760 and the teachings thereof are incorporated herein. By reference to FIGS. 2 through 5 and by further reference to the teachings of my prior '760 patent, like numbered parts functioning in the like manner to that previously described, the inventive system generally designated by the numeral 110 includes a generally rectangular gas impervious chamber 120 defined by a flat transparent front panel 121 peripherally bonded to the edges of a mating concave rear panel 122 to form a closed cavity 123 therebetween. A conductor 125 is then extended along the exterior of the rear panel 122 deploying a flat sheet electrode 126 over chamber 120 under a sealing membrane 124 adhered to the edges of rear panel 122.

Figure 2:
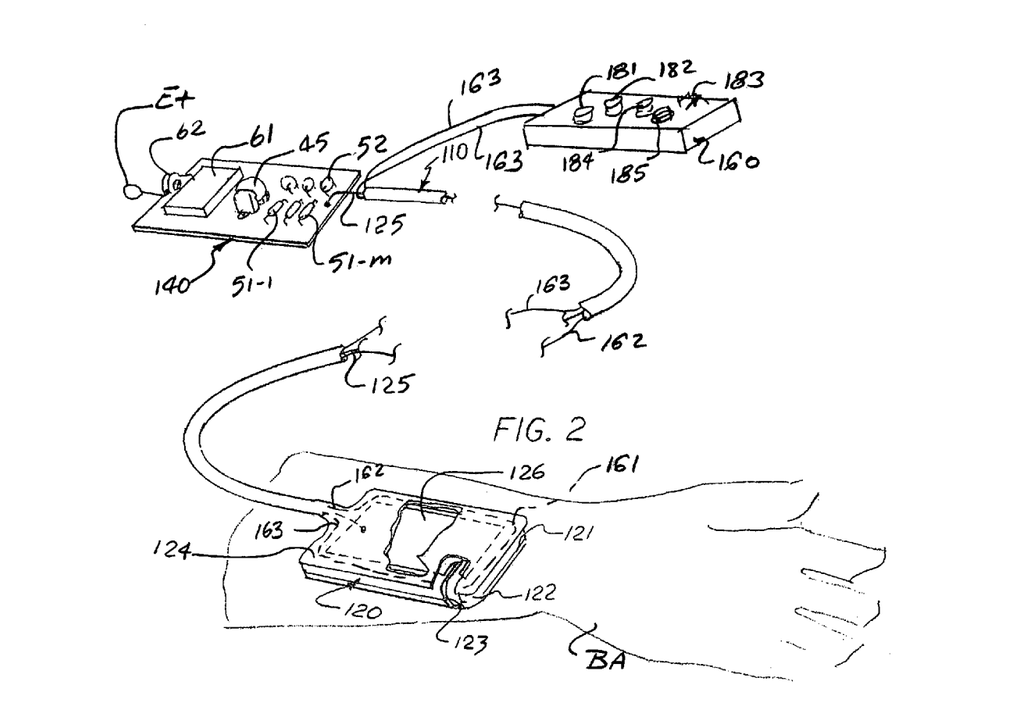
FIG. 2 is a perspective illustration, in partial sections, of the inventive system illustrating the positioning thereof adjacent a selected portion of a user's anatomy.
Figure 3:
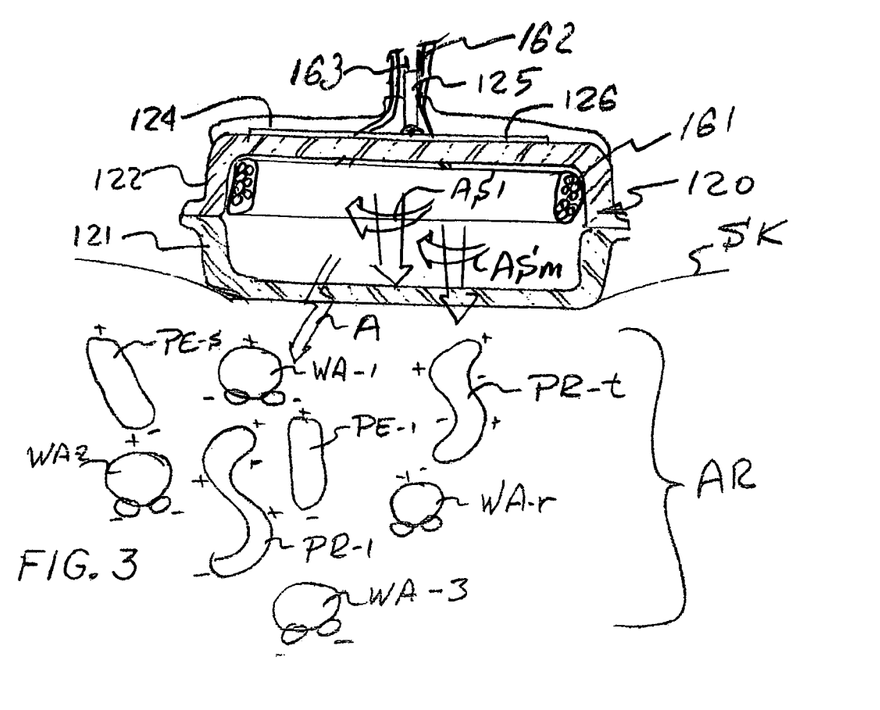
FIG. 3 is an exemplary electro-potential lattice approximating the polar nature of human tissue that is exposed both to a charged field and to light stimulation.
Figure 4:
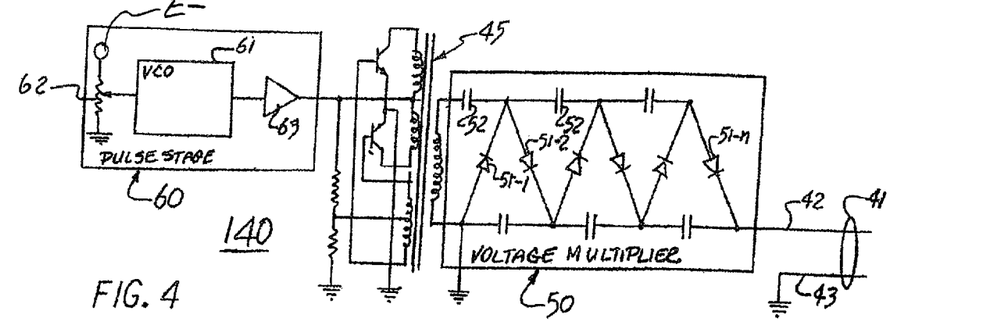
FIG. 4 is a circuit diagram of a pulsed charge circuit useful with the present invention.
Figure 5:
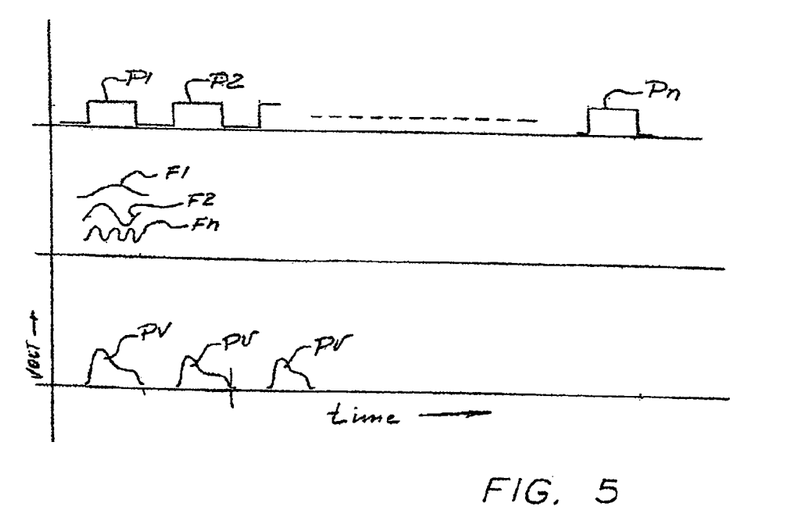
FIG. 5 is a diagrammatic illustration of the pulse shapes provided by the circuit shown in FIG. 4.

Similar to the teachings of my prior '760 patent chamber 120 may be filled with a gaseous mixture of common molecules like water vapor, carbon dioxide, carbonic acid and the like, each readily brought to a higher excitation state by electrical charge of electrode 126. To develop this charge potential the other end of conductor 125, in turn, connects to a pulsed power source generally designated 140 comprisng a pulse stage 60 of similar construction to that shown by the same numeral in my prior '760 patent, gated by a voltage controlled oscillator 61 set in its oscillation frequency by a potentiometer 62 in a voltage divider circuit between the positive signal E− and ground. The output of oscillator 61 drives to saturation at both limits of an operational amplifier 63 which is then amplified by a power amplifier 65 that is tied to the primary of a transformer 45 the secondary thereof driving a voltage multiplier 150 comprising a lattice of diodes 51-1 through 51-m interconnected by capacitors 52 with the last doubler stage at diode 51-m then connecting to the conductor 125.

In accordance with the present invention the pulse potential EF of conductor 125 is well below the ionization level of the gases in cavity 123 but is sufficient to exceed the bonding potential of the typical outer electrons of organic molecules, e.g., voltages less than 50 volts. Thus only singular electromagnetic wavelengths A associated with electron state change are emitted, particularly those containing the spectra of the common molecular states.

It will be appreciated by those skilled in the art that the foregoing pulse circuit is configured substantially like the pulse circuit in the '760 patent. By reducing the number of multiplication stages, however, the effective potential is substantially below that resulting in ionizing disassociation and the effect is primarily one of electric potential or charge. By particular reference to FIG. 3 this charge effect couples with the polar molecules like water WA-1 through WA-r, other polar organic molecules like peptides PE-1 through PE-s, proteins PR-1 through PR-t and so on. In the presence of an electric charge field these will arrange in lattices or arrays AR where the polar difference across this molecular array in the tissue and the molecular lattice of the gas within cavity 123 is less than the potential EF at the electrode 126. The excess electrode potential is then useful to effect an electron state change along with the associated shedding of light that may then cascade to excite corresponding molecules WA-1 through WA-r in the tissue structure.

Figure 6:
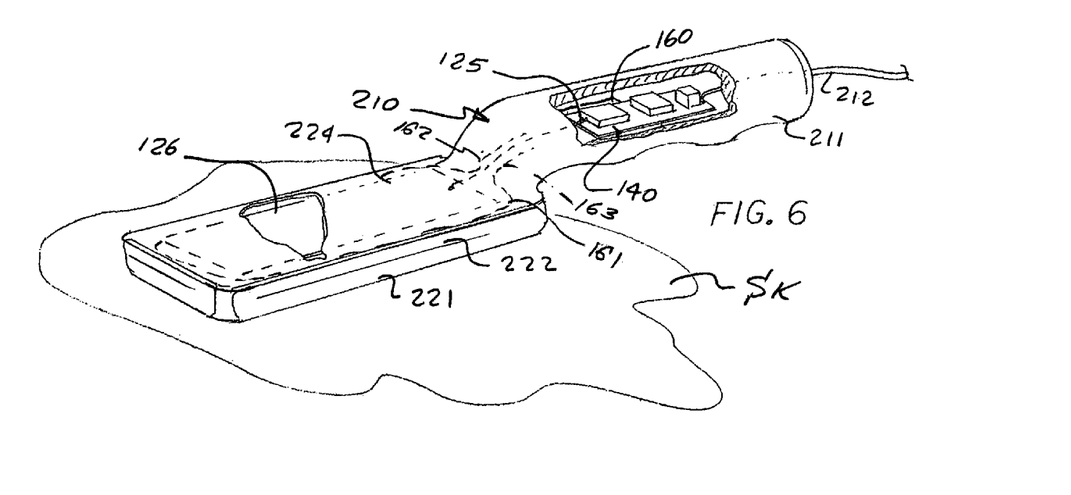
FIG. 6 is a perspective illustration, in partial section, of one physical configuration of the inventive pulse charge system conformed as a manual applicator of a geometry that provides the dominant discharge path across the charged cavity.

Those skilled in the art will appreciate that the foregoing inventive system includes inherent discharge preferences that seek out the shortest discharge paths. To confine these discharge effects to a path across chamber 120, and preferably not across the conductor 125 to ground, an applicator structure is illustrated in FIG. 6 under the generally numbered designation 210 in which like numbered parts function in like manner to those previously described. More precisely, applicator 210 is characterized by a generally cylindrical handle 211 of a substantial radial and longitudinal dimension and a dielectric material selected to insulate the pulsed power source 140 including all the operative components thereof. An electrical lead 212 then extends into handle 211 to provide the power signal E+ to circuit 140 which then generates the sequence of pulses on the output conductor 125 and the rectangular sheet electrode 126. Chamber 120 is formed on the interior of an offset rectangular piece 221 extending in cantilever from handle 211 with the electrode 126 mounted on the rear surface 222 thereof and thereafter sealed by an exterior membrane 224 in this deployment. The front surface 223 of piece 221 can then be manipulated into any desired contact alignment with the skin SK of the user. By selecting the material dielectric coefficients and geometric spacing dimensions this structure insures that the minimal discharge path is across chamber 120, thus insuring that the user's hand UH does not by-pass the desired effect. In this manner the primary result is the one previously described, a result that assists in realigning the various molecular lobe structures of the biological molecules affected.

Figure 7:
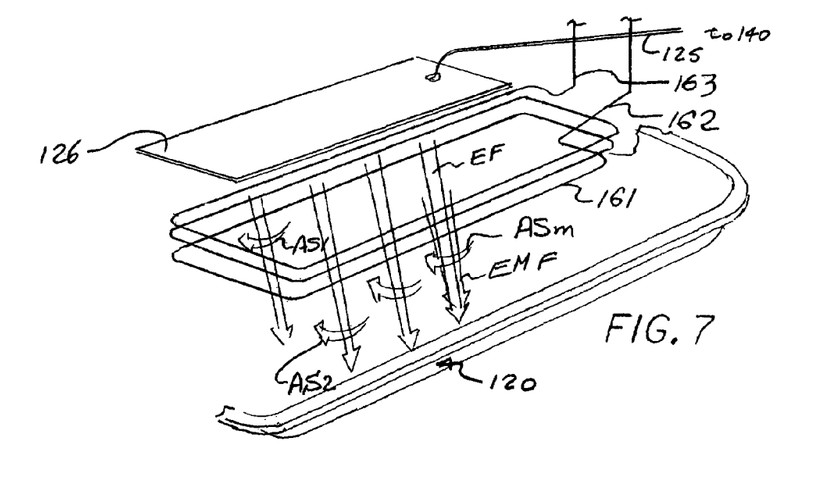
FIG. 7 is yet a further perspective illustration depicting an electrically pulsed coil deployed in a surrounding alignment about the charged electrode of the device shown in FIGS. 2 through 6 for developing a right hand spin polarizing electromagnetic field useful in aligning the vectors of the emissions associated with the change in the electron states effected by the electrical charge.

I have further found that the foregoing effect can be greatly enhanced by concurrently polarizing the common vectors of each of the emitted light energy in cascade into an alignment along with the charge field vector. To provide this right hand spin polarization an electromagnetic field is developed in accordance with the illustrations in FIGS. 7-9, wherein like numbered parts function in like manner to that previously described. More precisely, a coil 161 is wound around the interior periphery of chamber 120 in a plane generally parallel to the plane of the sheet electrode 126 in either one of the two applicator forms 10 and 210, with the ends 162 and 163 of the coil then connected across yet another pulse circuit 160 exemplified by the implementation shown in FIG. 9, wherein an oscillator circuit is formed by cross coupling the collector to base connections between two transistors 181 and 182 with the base bias of transistor 182 controlled by a potentiometer 183 which, in combination with the other resistors R1, R2 through Rs and capacitors C1 and C2, set the desired oscillation frequency. The collector of transistor 182 then drives the base of a transistor 184 in a switching circuit formed by gating a transistor 185 in and out of conduction in a circuit connection between the coil end 163 and ground, with the other end 162 of coil winding 161 connected to the power source E+. In this manner a generally square wave pulse sequence is developed across the coil, producing an electromagnetic field vector EMF aligned generally orthogonally to the plane of the sheet electrode 126 and cavity 120 and coinciding with the emitted radiation field vector EF.

Figure 8:
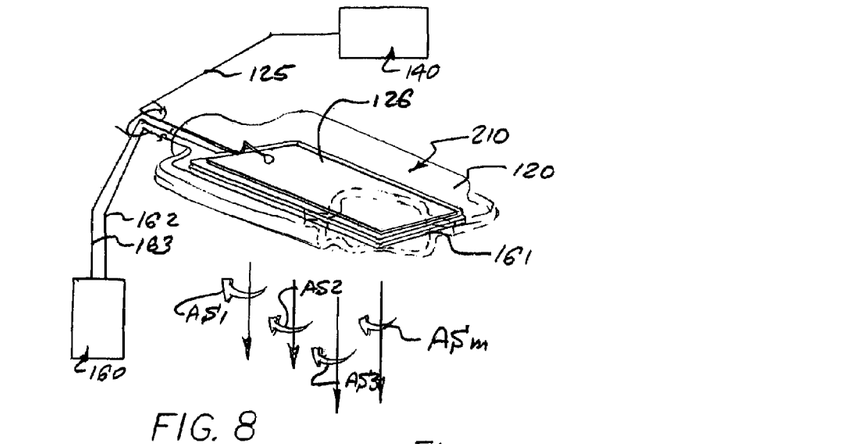
FIG. 8 is a diagrammatic illustration of the combined effects at the inventive intersection of the charge field within the electromagnetic to polarize the light energy emitted in the course of the electron state change along a common vector exemplified in an alignment useful in treating macular degeneration.
Figure 9:
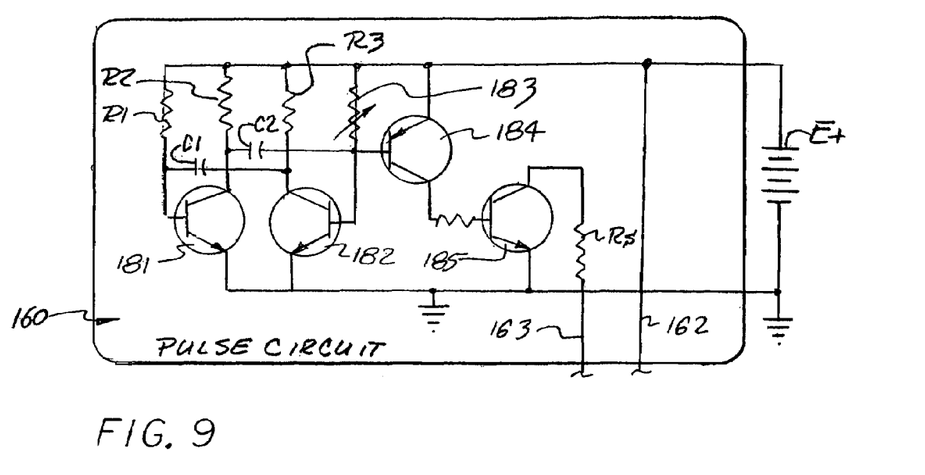
FIG. 9 is a further circuit diagram of a pulse circuit useful in developing the electromagnetic field.

By particular reference to FIG. 8, the electromagnetic field vector EMF imposes a corresponding uniformly aligned right hand spin to the spectra A emitted by the constituent elements like O, C, H and N both within chamber 120 and also in the adjacent tissue, shown symbolically as the electromagnetic wavelengths right hand spin vectors AS1 through ASm. By well known principles of physics this coherent realignment of the spin vectors is obtainable without any energy exchange, thus promoting a generally uniform, polarized cascade through the tissue array AR in the course of their emission and absorption that has little or no collateral energy exchange associated therewith. I have found that electromagnetic field levels as low as 0.7 Gauss are sufficient for effective penetration of the field EMF through the adjacent tissue. Thus the major risks associated with high energy irradiation are minimized by limiting both the magnetic flux and the relative electric potential of the electrode 120 to 50 volts. In this manner irradiation of sensitive biological elements, like those in the human eye, is rendered safe allowing for the charge realignments and correction of all-trans retinal molecules, peptides, proteins and chromosomes.

The usefulness of this irradiation process has had received extensive verification in the course of Phase Two clinical trials recently conducted to verify the therapeutic efficacy of the inventive device in treating Age-Related Macular Degeneration [AMD], Diabetic Retinopathy and Retinitis Pigmentosa, all retinal diseases with few known treatment modalities. Periodic irradiation of the retina of AMD patients, for example, directly through the eye lens, in 20 minute intervals, has shown measurable improvement in visual acuity as measured by the Vector Vision LogMar instrumentation with one improvement as high as 57% and an improvement average of 16%. Even higher treatment averages were obtainable with a patient population that was limited to early-stage AMD, with visual acuity improvement averages as high as 33%.

Figure 10A:
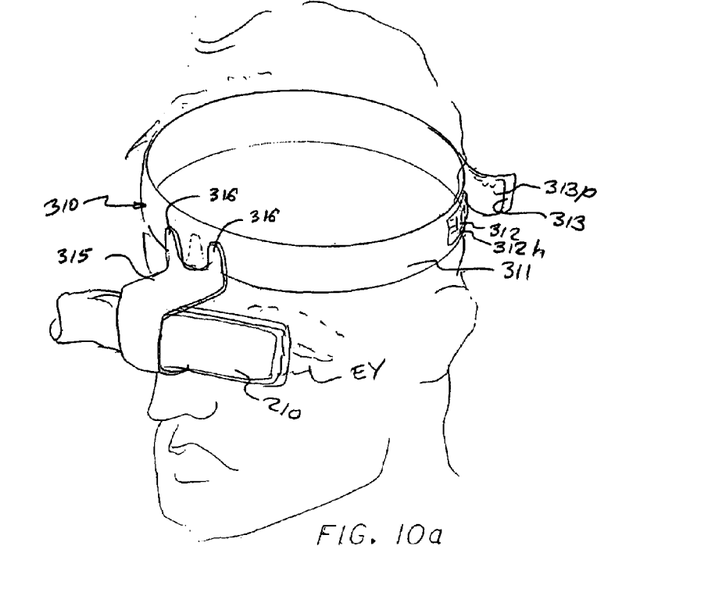
FIGS. 10a and 10b are further perspective illustrations of exemplary holding structures for aligning the inventive charge system adjacent selected portions of human anatomy.
Figure 10B:
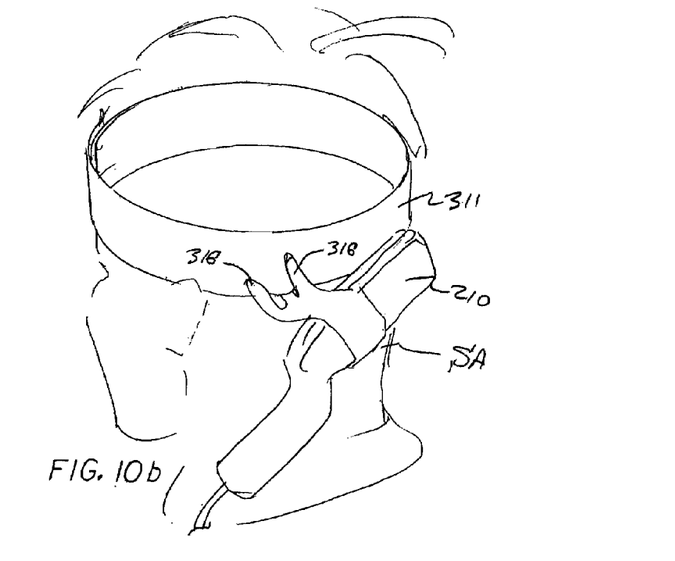

By reference to FIGS. 10a and 10b this irradiation treatment of the retina can be rendered convenient by a holding structure generally designated by the numeral 310, comprising a generally circular strap 311 provided with overlapping ends 312 and 313 engageable to each other by opposing hook and pile segments, like those sold under the mark "VELCRO", respectively shown as end segments 312h and 313p, to form a hoop of various peripheral dimensions. A holding bracket 315 may then be selectively clipped to the strap 311 by interlaced engagement thereof between offset tines 316 extending therefrom to deploy the applicator structure 210 over and adjacent to the anatomical area that is to be irradiated. As exemplified in FIGS. 8 and 10a strap 311 is positioned about the circumference of a head of a patient with the holding bracket 315 then clipped to the strap 311 over the forehead to extend over the patient eyes EY with the irradiation then focused by the eye lens EL onto the retina ER. With this assistance the applicator structure 210 can be conveniently held right over the eyes for the necessary durations determined by any treatment regimen. Alternatively, as illustrated in FIG. 10b the bracket is clipped to the strap 311 in alignment over the anterior surfaces of the skull SA containing the visual cortex.

It is believed that by way of this polarized irradiation small biological structures like the walls of the 0.8 micron diameter capillary bed of the retinal macula RM are charged to an equal polarity, thus promoting wall separation for an increased flow. In consequence, circulation for nourishment and removal of by-products is re-established, resolving the principal source for the pathology of macular degeneration. I have further observed that this process is rendered particularly effective in the spectral emission and reabsorption of hydrogen in the 450 nanometer emission band, suggesting the involvement of the hydrogen atom via the All-trans-Retinal in the cones of the macula RM. This is consistent with the generally observed deterioration with age in the retinal perception of the blue color, now regenerated by this inventive process, thereby restoring the full visual range from the ultraviolet to the infrared. Of course, similar benefits should follow in other biological structures.

By this simple expedient the device can be variously deployed over the body of the patient, resolving most degenerative molecular malformations in the targeted tissue. Of course, other shapes of the applicator structure 210 may be devised with particular attention to the body shape that is intended for exposure, such as cavities convolved into toroidal shapes to surround a digit or limb or similar adaptations. In each instance, however, the geometric constraint that needs to be met is one that assures that the minimal discharge path is across the cavity.

Figure 11:
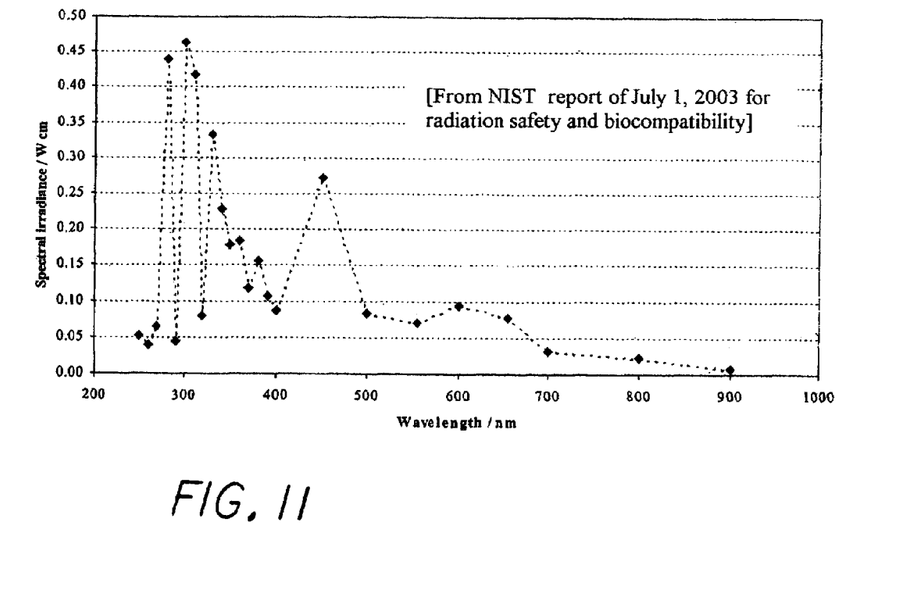
FIG. 11 is a graphical illustration of the spectral distributions of the electromagnetic wavelength spectra emitted in the course of use of the instant invention.

By reference to FIG. 11 the spectral distribution of the emissions from chamber 120 has been confirmed by actual measurement including the several spectral peaks SP1-SPq associated with biological matter and also the very pronounced hydrogen emission spectrum peak HSP at 450 nanometer emission band referenced above. Thus the theoretically inferred results are directly confirmed by measurement which has been thereafter further confirmed by clinical trials. Thus a conveniently deployed, relatively safe treatment mechanism is devised which is broadly useful in realigning the molecular architecture, and therefore the local charges, of living matter Obviously, many modifications and variations can be effected without departing from the spirit of the invention instantly disclosed. It is therefore intended that the scope of the invention be determined solely by the claims appended hereto.

It is claimed:

1. An applicator useful in inducing an increase in the charge state of biological molecules comprising living tissue, comprising:
    a generally rectangular hollow chamber defined by a front wall and an opposed rear wall enclosing a volume of gas confined therebetween;
    a planar electrode affixed to the exterior of said chamber in contiguous alignment adjacent said rear wall, said electrode including a conductor connected thereto;
    an electrically conducting coil mounted on the exterior periphery of said chamber in a plane generally parallel to said planar electrode, said coil including a first and second electrical terminal at the ends thereof;
    first electrical pulse means connected to said conductor for producing a sequence of first electrical pulses of an electrical potential relative the ambient charge level sufficient to excite selected ones of the molecules comprising said volume of gas to a higher level of excitation, each said occurrence of energy change producing a discrete electromagnetic emission; and
    second electrical pulse means for producing a sequence of second electrical pulses conducted through said coil to periodically generate a clockwise magnetic flux field along a vector generally orthogonal to the plane of said coil, said second electrical pulse means being connected across said first and second electrical terminals.

2. Apparatus according to claim 1, wherein:
    said front and rear walls of said chamber are formed of a translucent material.

3. Apparatus according to claim 2, wherein:
    said chamber is conformed for intimate contact with the skin of a person at the front wall thereof.

4. Apparatus according to claim 3, further comprising:
    an insulating handle attached to said chamber and conformed to enclose said conductor therein, whereby the preferred path of electrical discharge between said conductor, said electrode and said tissue is across said chamber.

5. A pulsed charge applicator useful in inducing en increase in the electrical charge state of a biological molecule in human tissue, comprising:
    a generally rectangular hollow chamber defined by a transparent front wall and an opposed rear wall enclosing a volume of gas confined therebetween, said chamber being confined for intimate contact with the tissue of a person at the front wall thereof;
    a planar electrode affixed to the exterior of said chamber in coutiguous alignment adjacent said rear wait said electrode including a conductor connected thereto;
    an insulating handle attached to said chamber and conformed to enclose said conductor therein, whereby the preferred path of electrical discharge between said conductor, said electrode and said tissue is across said chamber;
    an electrically conducting coil mounted on the exterior periphery of said chamber in a plane generally parallel to said planar electrode, said coil including a first and second electrical terminal at the ends thereof;
    first pulse charge means connected to said conductor for producing a sequence of electrical charge pulses of an electrical potential relative the ambient charge level sufficient to excite selected ones of the molecules comprising said volume of gas to a higher level of excitation, each said occurrence of energy change producing a discrete electromagnetic pulse; and
    second electrical pulse means for producing a sequence of second electrical pulses conducted through said coil to periodically generate a clockwise magnetic flux field along a vector generally orthogonal to the plane of said coil, said second electrical pulse means being connected across said first and second electrical terminals.

6. Apparatus according to claim 5, wherein:
    said volume of gas includes molecules of water.

7. Apparatus according to claim 6, wherein:
    said volume of gas includes molecules of carbon dioxide.

8. Apparatus according to claim 7, wherein:
said first pulse means includes voltage doublers.

9. Apparatus for inducing a change in the local electrical charge of living tissue, comprising:
- an electrical circuit conformed to produce a sequence of first electric pulses each of an electrical potential sufficient to excite a selected gas molecule to a higher level of excitation and thereby producing a right hand spin electromagnetic pulse associated therewith;
- a generally flat hollow chamber defined by a translucent front wall and an opposed rear wall enclosing a volume of gas confined therebetween, said gas including said selected gas molecules;
- a planar electrode affixed to the exterior of said chamber in contiguous alignment adjacent said rear wall, said electrode including a conductor connected to said electrical circuit, whereby said right hand spin electromagnetic pulses produced in said chamber are communicated into said tissue;
- an electrically conducting coil mounted on the exterior periphery of said chamber in a plane generally parallel to said planar electrode, said coil including a first and second electrical terminal at the ends thereof; and
- electrical pulse means for producing a sequence of second electrical pulses conducted through said coil to periodically generate a clockwise magnetic flux field along a vector generally orthogonal to the plane of said coil, said electrical pulse means being connected across said first and second electrical terminals.

10. Apparatus according to claim 9, further comprising:
an insulating handle attached to said chamber and conformed to enclose said electrical circuit and conductor therein, whereby the preferred path of electrical discharge between said conductor, said electrode and said tissue is across said chamber.

11. Apparatus according to claim 9 wherein:
said volume of gas includes molecules of water.

12. Apparatus according to claim 11, wherein:
said volume of gas includes molecules of carbon dioxide.

* * * * *